US 6,719,688 B2

(12) United States Patent
Pecherer et al.

(10) Patent No.: US 6,719,688 B2
(45) Date of Patent: Apr. 13, 2004

(54) LIGHT GUIDE MOUNT FOR USE WITH A LARYNGOSCOPE

(75) Inventors: Eugeny Pecherer, Netanya (IL); Igor Kobets, Pardes Hanna (IL)

(73) Assignee: Truphatek International Limited, Netanya (IL)

( * ) Notice: Subject to any disclaimer, the term of this patent is extended or adjusted under 35 U.S.C. 154(b) by 12 days.

(21) Appl. No.: 10/025,481

(22) Filed: Dec. 26, 2001

(65) Prior Publication Data

US 2003/0120131 A1 Jun. 26, 2003

(30) Foreign Application Priority Data

Nov. 19, 2001 (IL) .................................................. 146569

(51) Int. Cl.$^7$ ................................................ A61B 1/06
(52) U.S. Cl. ........................ 600/199; 600/188; 600/193
(58) Field of Search ................................. 600/185, 188, 600/190, 191, 193, 199

(56) References Cited

U.S. PATENT DOCUMENTS

| 4,437,458 A | 3/1984 | Upsher |
| 4,570,614 A | 2/1986 | Bauman |
| 4,958,624 A | 9/1990 | Stone et al. |
| 5,060,633 A | * 10/1991 | Gibson |
| 5,529,570 A | 6/1996 | Storz ........................... 600/199 |
| 6,139,491 A | 10/2000 | Heine et al. ................. 600/199 |
| 6,213,937 B1 | 4/2001 | Vivenzio ..................... 600/199 |

OTHER PUBLICATIONS

Hilbro brochure, Green System Fiber Optic Laryngoscope, Interchangeable Light Guide Insert, Oct. 2001.
Medizintechnik KaWe Germany, Laryngoskope, Megalight F.O.

* cited by examiner

*Primary Examiner*—Cary E. O'Connor
(74) *Attorney, Agent, or Firm*—Nath & Associates PLLC; Harold L. Novick

(57) ABSTRACT

A light guide mount for use with a Shucman™ type ISO 7376/1 compatible laryngoscope blade, the light guide mount including a housing with a throughbore, and an L-shaped fiber optic light pipe with a short leg securely fastened into the housing and a long leg for extending along the blade, the throughbore accommodating a floating contact pin, a portion of the short leg, and a miniature bulb interdisposed between the contact pin and the short leg. A removable light guide mount for use with a laryngoscope blade, the light guide mount being removably slidingly insertable into a suitably shaped and dimensioned slot formed in a base portion of the blade, and secured therein by an inter-engagement means, and preferably a snap-fit inter-engagement means.

20 Claims, 5 Drawing Sheets

US 6,719,688 B2

LIGHT GUIDE MOUNT FOR USE WITH A LARYNGOSCOPE

FIELD OF THE INVENTION

The invention is in the field of laryngoscopes in general, and light guide mounts for use with laryngoscopes in particular.

BACKGROUND OF THE INVENTION

Laryngoscopes can be generally classified into two types as follows: ISO 7376/1 compatible laryngoscopes having a miniature bulb disposed in their blades, and ISO 7376/3 compatible laryngoscopes having a miniature bulb disposed in their handles. ISO 7376/1 compatible laryngoscopes can fitted with either one of two types of laryngoscope blades as follows: the conventional type with an incandescent miniature bulb disposed adjacent the tip of the blade and the more recent Shucman™ type having often a fragile halogen miniature bulb disposed in the rear portion of the blade, for example, as illustrated and described in U.S. Pat. No. 4,437,458 to Upsher, and as commercially available from Truphatek International Ltd, Netanya, Israel. Removable fiber optic light pipes have been proposed for ISO 7376/3 compatible laryngoscopes for sterilization and replacement purposes, for example, as illustrated and described in U.S. Pat. No. 4,570,614 to Bauman, U.S. Pat. No. 4,958,624 to Stone et al, U.S. Pat. No. 5,529,570 to Storz, U.S. Pat. No. 6,139,491 to Heine et al, and U.S. Pat. No. 6,213,937 to Vivenzio.

SUMMARY OF THE INVENTION

The first aspect of the present invention is for a novel light guide mount including a miniature bulb for use with a Shucman™ type laryngoscope blade which satisfies the needs of ready component part removable for both sterilization and replacement purposes, longevity by avoiding electrical components susceptible to corrosion, and ready manufacturability. The light guide mount can be integrally formed with a laryngoscope blade to render a fiber optic laryngoscope blade designed for either single or multi-patient use. But preferably the light guide mount including its often fragile miniature bulb can be a discrete removable component again designed for either single or multi-patient use.

The second aspect of the present invention is for a novel removable light guide mount for use with a laryngoscope which satisfies the needs of ready detachment for both sterilization and replacement purposes, and ready manufacturability. The inter-engagement means employed for securing a light guide mount to a laryngoscope blade is preferably of the snap-fit type but alternative inter-engagement means may include a screw arrangement, and the like. A light guide mount can be designed for fitting an ISO 7376/1 compatible laryngoscope blade of either the conventional type or the Shucman™ type, or an ISO 7376/3 compatible laryngoscope blade, and it also can be designed for either single or multi-patient use.

BRIEF DESCRIPTION OF THE DRAWINGS

In order to understand the invention and to see how it can be carried out in practice, a preferred embodiment will now be described, by way of a non-limiting example only, with reference to the accompanying drawings, in which similar parts are likewise numbered, and in which.

DETAILED DESCRIPTION OF THE DRAWINGS

Figure 1:
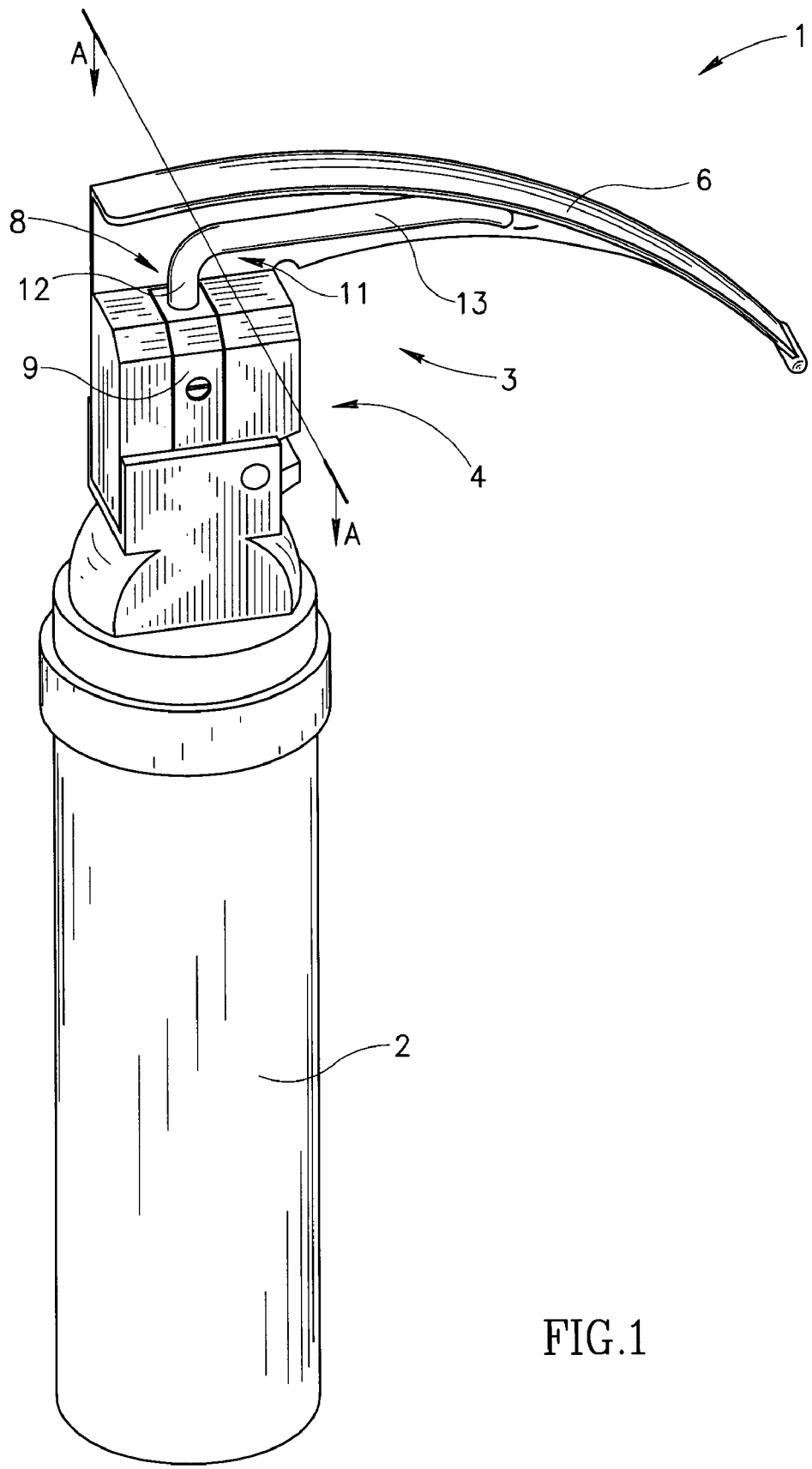
FIG. 1 is a pictorial view of an ISO 7376/1 compatible laryngoscope with a Shucman™ type laryngoscope blade having a removable light guide mount in accordance with the present invention.

FIG. 1 shows an ISO 7376/1 type laryngoscope 1 including a laryngoscope handle 2, and a Shucman™ type laryngoscope blade 3 having a base portion 4 and a spatula 6 transversely extending from the laryngoscope handle 2 on the removable secure coupling of the base portion 4 on the laryngoscope handle 2 for insertion into a patient's mouth for illuminating its interior. The coupling means for coupling the base portion 4 on the laryngoscope handle 2 is in accordance with the ISO 7376/1 standard, and therefore is not described herein for the sake of conciseness. The base portion 4 has an elongated slot 7 (see FIG. 4) co-directional with the laryngoscope handle 2 on coupling the base portion 4 thereon for receiving a light guide mount 8. The light guide mount 8 has a housing 9 and an L-shaped fiber optic light pipe 11 with a short leg 12 securely fastened into the housing 9, and a long leg 13 extending along the spatula 6 towards its tip.

Figure 2:
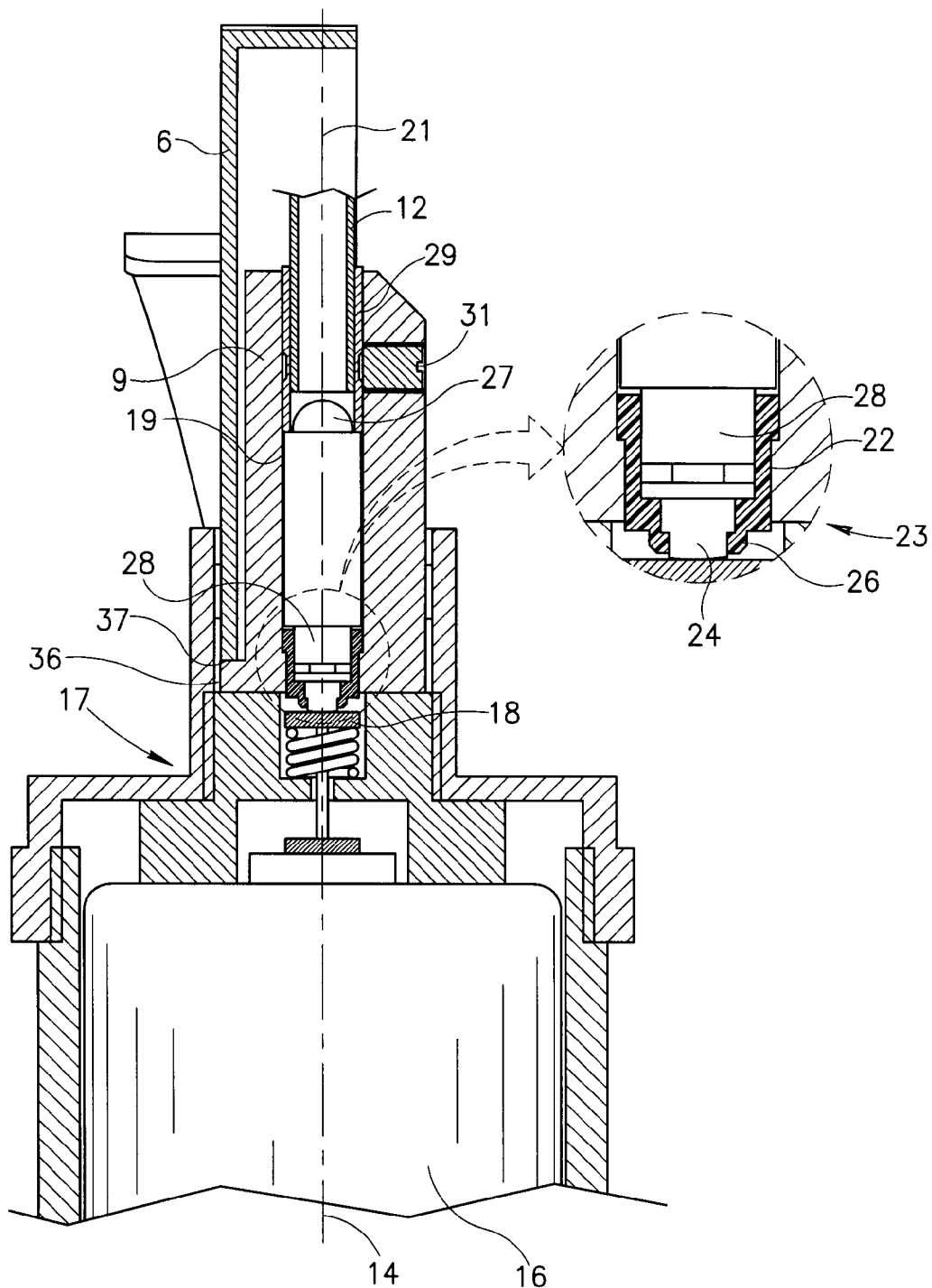
FIG. 2 is a cross sectional view of the laryngoscope of FIG. 1 along line A—A in FIG. 1.

FIG. 2 shows that the laryngoscope handle 2 has a longitudinal axis 14, a battery 16 (constituting an electrical power source), and a cartridge 17 with a reciprocal electrical contact 18 normally spring biased away from the battery 16 and in electrical connection therewith (as seen in FIG. 2) on secure coupling of the base portion 4 on the laryngoscope handle 2. The housing 9 has a throughbore 19 with a longitudinal axis 21 co-axial with the laryngoscope handle's longitudinal axis 14 on coupling the base portion 4 on the laryngoscope handle 2. The throughbore 19 has a narrow neck portion 22 snugly accommodating a so-called floating contact pin 23 having a contact pin 24 inserted in a flexible plastic bushing 26. The throughbore 19 contains a halogen miniature bulb 27 with its electrical contact 28 juxtaposed against the contact pin 24, and the end of the fiber optic light pipe's short leg 12 inserted into a sleeve 29 against which bears a fastener 31 for ensuring tight electrical contact between the electrical contact 28 and the contact pin 24. Access to the miniature bulb 27 for replacement purposes merely involves unscrewing the fastener 31 and removing the fiber optic light pipe's short leg 12 from the housing 9.

Figure 3:
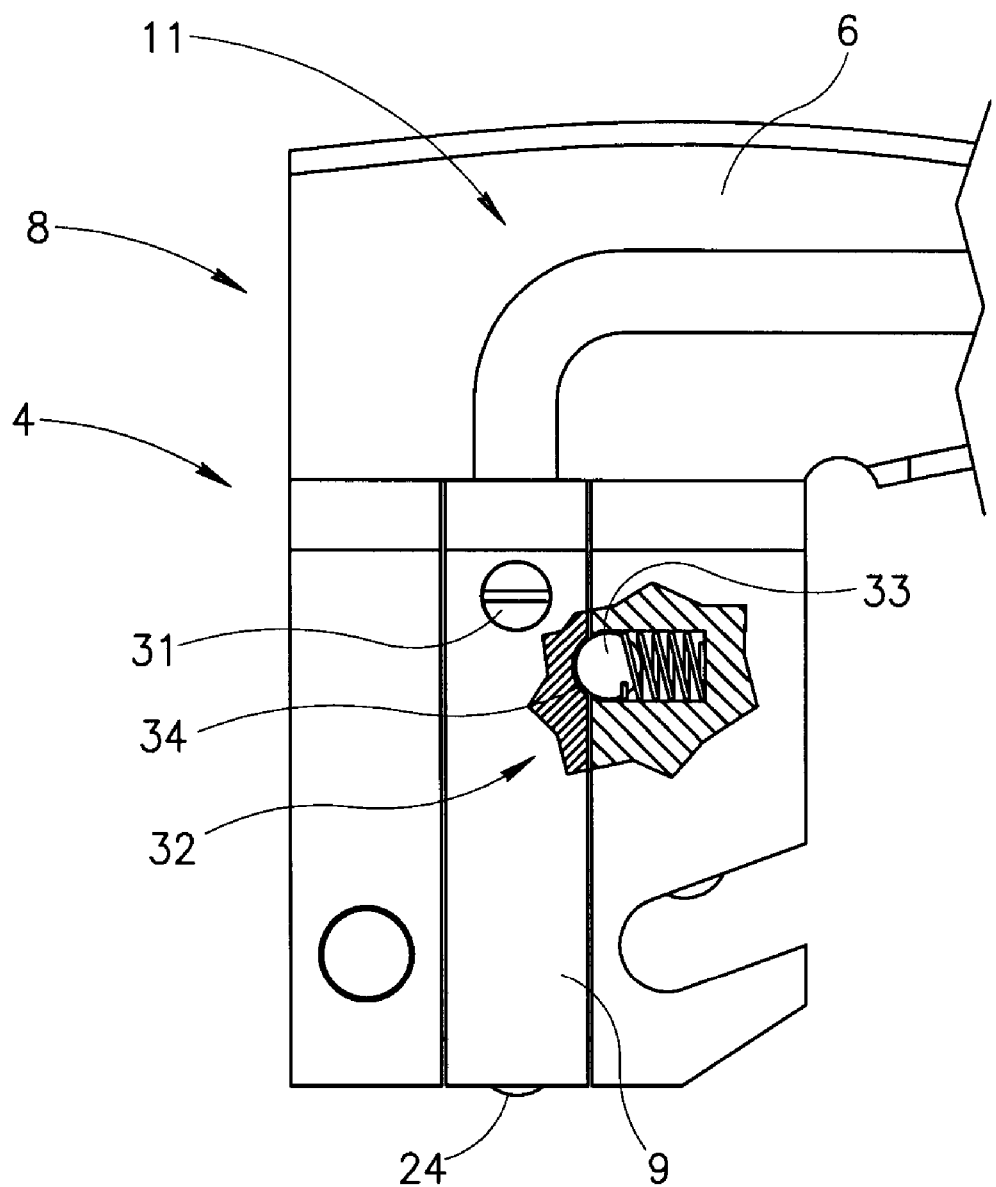
FIG. 3 is a partially cut-away front view of the laryngoscope of FIG. 1.

FIG. 3 shows that the body portion 4 and the housing 9 are each provided with one component of a snap-fit inter-engagement means 32 for tightly securing the light guide mount 8 in the laryngoscope blade 3 on full insertion of the housing 9 into the slot 7. The snap-fit inter-engagement means 32 is implemented in the form of a spring biased ball detent 33 formed in one of the opposite side walls of the slot 7 for being positively urged into a recess 34 formed in the major surface of the housing 9 juxtaposed thereagainst on full insertion of the housing 9 into the slot 7.

The housing 9 is formed with a release tab 36 (see FIGS. 2 and 4) for being snugly received in a cutaway 37 formed in the base portion 4 on full insertion of the housing 9 in the slot 7 for facilitating the release of the light guide mount 8 from the laryngoscope blade 3. In addition, the release tab 36 acts as a stop for facilitating the correct positioning of the housing 9 within the slot 7 during assembly of the laryngoscope blade 3.

Figure 4:
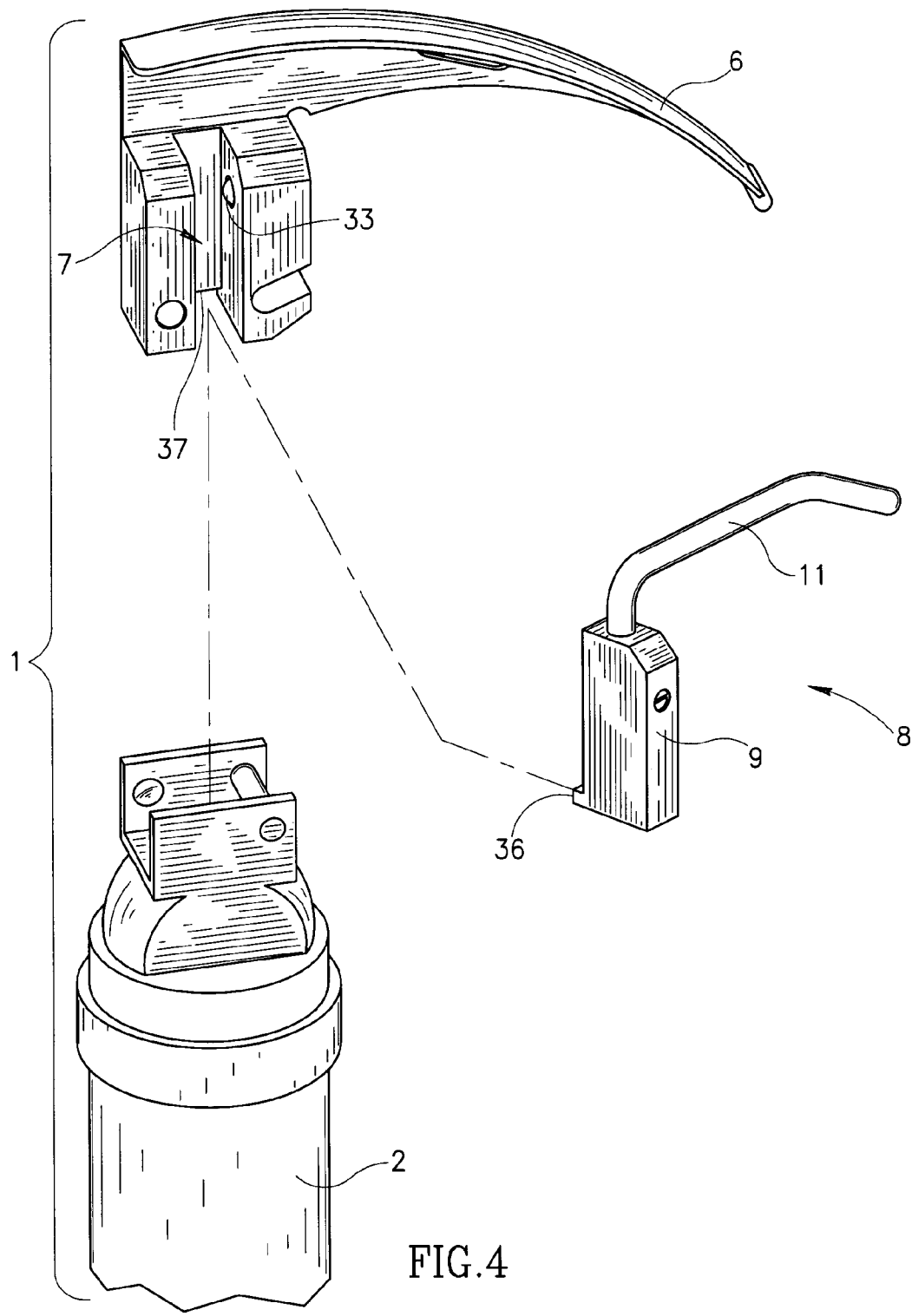
FIG. 4 is a pictorial view showing the assembly of the laryngoscope of FIG. 1.

FIG. 4 shows the assembly of the laryngoscope 1: The light guide mount 8 is fully inserted into the slot 7 such that its release tab 36 is snugly received in the cutaway 37 and the ball detent 33 is positively urged in the recess 34 for securing the light guide mount 8 to the laryngoscope blade 3. The laryngoscope blade 3 is securely coupled on the laryngoscope handle 2 whereupon the contact pin 24 depresses the electrical contact 18 for energizing the miniature bulb 27 for illuminating via the fiber optic light pipe 11 the interior of a patient's mouth on insertion of the spatula 6 thereinto.

Figure 5:
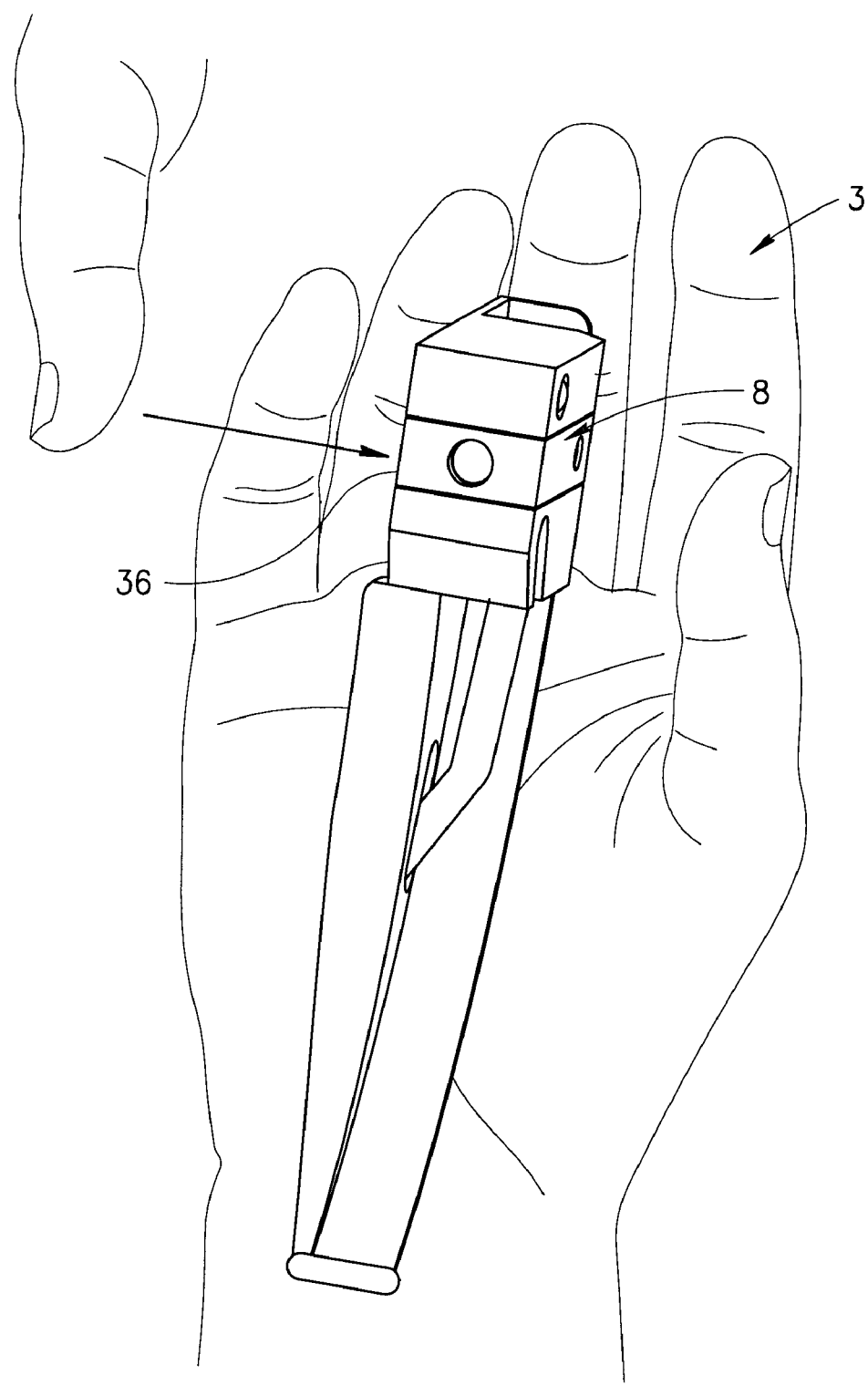
FIG. 5 is a pictorial view showing the release of the light guide mount from the Shucman™ type laryngoscope blade of FIG. 1.

FIG. 5 shows the release of the light guide mount 8 from the laryngoscope blade 3: The laryngoscope blade 3 is initially removed from the laryngoscope handle 2 whereupon a user applies pressure with his thumb against the release tab 36 thereby releasing the light guide mount 8 from the laryngoscope blade 3.

While the invention has been described with respect to a limited number of embodiments, it will be appreciated that many variations, modifications, and other applications of the invention can be made within the scope of the appended claims.

What is claimed is:

1. Light guide mount for use with an ISO 7376/1 compatible laryngoscope blade having a base portion for removable secure coupling on an ISO 7376/1 compatible laryngoscope handle having a longitudinal axis, an electrical power source and a reciprocal electrical contact normally biased away from the electrical power source and in electrical connection therewith on secure coupling of the base portion thereon, and a spatula transversely extending from the laryngoscope handle on the secure coupling of the base portion thereon for insertion into a patient's mouth,
   the light guide mount comprising
   (a) a housing for removable sliding insertion into a suitably shaped and dimensioned slot formed in the base portion and co-directional with the laryngoscope handle on secure coupling of the base portion thereon, and
   (b) an L-shaped light pipe with a short leg securely fastened into said housing and a long leg for extending along the spatula towards its tip,
   said housing having a throughbore with a longitudinal axis substantially parallel with the laryngoscope handle's longitudinal axis on secure coupling of the base portion thereon, and a component of an inter-engagement means for enabling the removable securing of the light guide mount to the laryngoscope blade,
   said throughbore accommodating a floating contact pin, a portion of said short leg, and a miniature bulb interdisposed between said contact pin and said portion of said short leg,
   the arrangement being such that said miniature bulb is energized on secure coupling of the base portion on the laryngoscope handle for illuminating via said light pipe the interior of the patient's mouth on insertion of the spatula thereinto.

2. The mount according to claim 1 wherein said throughbore has a narrow neck portion for snugly accommodating said contact pin, and said housing includes a fastener for bearing against said portion of said short leg fastened therein in a transverse direction with respect to said throughbore's longitudinal axis for securing said miniature bulb against said contact pin.

3. The mount according to claim 1 wherein said component is constituted by a recess in a major surface of said housing for receiving a spring biased ball detent provided in a side wall of the slot and positively urged thereinto on full insertion of said housing into the slot, said recess and the ball detent rendering in combination a snap-fit inter-engagement means for enabling the removable securing of the light guide mount to the laryngoscope blade.

4. The mount according to claim 1 wherein said housing has a release tab for being snugly received in a suitably sized and dimensioned cutaway in the base portion on full insertion of said housing in the slot, said release tab having an exposed surface on detachment of the base portion from the laryngoscope handle for enabling thumb pressure to be readily applied thereto for releasing the light guide mount from the laryngoscope blade.

5. The mount according to claim 1 and designed for single patient use.

6. An ISO 7376/1 compatible laryngoscope blade for use with an ISO 7376/1 compatible laryngoscope handle having a longitudinal axis, an electrical power source and a reciprocal electrical contact normally biased away from the electrical power source and in electrical connection therewith on secure coupling of an ISO 7376/1 compatible laryngoscope blade thereon,
   the blade comprising a base portion for removable secure coupling on an ISO 7376/1 compatible laryngoscope handle and a spatula transversely extending therefrom on the secure coupling of said base portion thereon for insertion into a patient's mouth,
   said base portion having a throughbore with a longitudinal axis substantially parallel with the laryngoscope handle's longitudinal axis on secure coupling of said base portion thereon, and an L-shaped light pipe with a short leg securely fastened into said base portion and a long leg for extending along the spatula towards its tip,
   said throughbore accommodating a floating contact pin, a portion of said short leg, and a miniature bulb interdisposed between said contact pin and said portion of said short leg,
   the arrangement being such that said miniature bulb is energized on secure coupling of said base portion on the laryngoscope handle for illuminating via said light pipe the interior of the patient's mouth on insertion of the spatula thereinto.

7. The blade according to claim 6 wherein said throughbore has a narrow neck portion for snugly accommodating said contact pin, and said base portion includes a fastener for bearing against said portion of said short leg fastened therein in a transverse direction with respect to said throughbore's longitudinal axis for securing said miniature bulb against said contact pin.

8. The blade according to claim 6 and designed for single patient use.

9. A removable light guide mount for use with a laryngoscope blade for removable secure coupling on a laryngoscope handle having a longitudinal axis and an electrical power source, the laryngoscope blade having a base portion including the light guide mount, and a spatula transversely extending from the laryngoscope handle on the secure coupling of the base portion thereon for insertion into a patient's mouth,
   the light guide mount comprising a housing removably slidingly insertable into a suitably shaped and dimensioned slot formed in the base portion and co-directional with the laryngoscope handle on coupling the base portion thereon, and having a component of an inter-engagement means for enabling the securing of said housing to the base portion, the arrangement being such that a miniature bulb of the laryngoscope is energized on the secure coupling of the base portion on the laryngoscope handle for illuminating the interior of the patient's mouth on insertion of the spatula thereinto.

10. The mount according to claim 9 wherein said component is constituted by a recess in a major surface of said housing for receiving a spring biased ball detent provided in a side wall of the slot and positively urged thereinto on full insertion of said housing into the slot, said recess and the ball detent rendering in combination a snap-fit inter-engagement means for enabling the removable securing of the light guide mount to the laryngoscope blade.

11. The mount according to claim 9 wherein said housing has a release tab designed to be snugly received in a suitably sized and dimensioned cutaway in the body portion on full insertion of said housing in the slot, said release tab having an exposed surface for enabling thumb pressure to be readily applied thereto for releasing the light guide mount from the laryngoscope blade.

12. The mount according to claim 9 and designed for removable secure coupling on an ISO 7376/1 compatible laryngoscope blade provided with a bulb for use with an ISO 7376/1 laryngoscope handle having a reciprocal electrical contact normally biased away from the electrical power source and in electrical connection therewith on secure coupling of the base portion on the laryngoscope handle.

13. The mount according to claim 12 wherein said housing is provided with an incandescent miniature bulb disposed adjacent the tip of the blade on insertion of the mount in the base portion of the laryngoscope blade.

14. The mount according to claim 12 wherein said housing has a throughbore with a longitudinal axis substantially parallel with the laryngoscope handle's longitudinal axis on secure coupling of the base portion thereon, and an L-shaped light pipe with a short leg securely fastened into said housing and a long leg for extending along the spatula towards its tip on insertion of the mount in the base portion of the laryngoscope blade, said throughbore accommodating a floating contact pin, a portion of said short leg and a miniature bulb interdisposed between said contact pin and said portion of said short leg.

15. The mount according to claim 14 wherein said throughbore has a narrow neck portion for snugly accommodating said contact pin, and said housing includes a fastener for bearing against said portion of said short leg fastened therein in a transverse direction with respect to said throughbore's longitudinal axis for securing said miniature bulb against said contact pin.

16. The mount according to claim 9 and designed for removable secure coupling on an ISO 7376/3 compatible laryngoscope blade for use with an ISO 7376/3 compatible laryngoscope handle having a miniature bulb energized on the secure coupling of the base portion on the laryngoscope handle thereon.

17. An ISO 7376/1 compatible laryngoscope blade comprising a base portion for removable secure coupling on an ISO 7376/1 compatible laryngoscope handle having a longitudinal axis, an electrical power source and a reciprocal electrical contact normally biased away from the electrical power source and in electrical connection therewith on secure coupling of said base portion thereon, and a spatula transversely extending from the laryngoscope handle on the secure coupling of said base portion thereon for insertion into a patient's mouth, said base portion including a slot co-directional with the laryngoscope handle on secure coupling of said base portion thereon for removably slidingly receiving a light mount guide therein, said light guide mount having (a) a housing with a throughbore having a longitudinal axis substantially parallel with the laryngoscope handle's longitudinal axis on its insertion into said base portion and the secure coupling of said base portion on the laryngoscope handle, and a component of an inter-engagement means for enabling the removable securing of said light guide mount to the laryngoscope blade, and (b) an L-shaped light pipe with a short leg securely fastened into said housing and a long leg for extending along said spatula towards its tip, said throughbore accommodating a floating contact pin, a portion of said short leg, and a miniature bulb interdisposed between said contact pin and said portion of said short leg, the arrangement being such that said miniature bulb is energized on secure coupling of said base portion on the laryngoscope handle for illuminating via said light pipe the interior of the patient's mouth on insertion of the spatula thereinto.

18. The blade according to claim 17 wherein a side wall of said slot is provided with a spring biased ball for being positively urged into a recess formed in a major surface of said housing on full insertion of said housing into said slot, said ball detent and said recess rendering in combination a snap-fit inter-engagement means for enabling the removable securing of said light guide mount to the laryngoscope blade.

19. The blade according to claim 17 wherein said base portion is formed with a cutaway for snugly receiving a release tab formed on said housing for enabling thumb pressure to be readily applied thereto for releasing said light guide mount from the laryngoscope blade on detachment of said base portion from the laryngoscope handle.

20. The blade according to claim 17 and designed for single patient use.

* * * * *